United States Patent
Arcand et al.

(10) Patent No.: US 9,717,582 B2
(45) Date of Patent: Aug. 1, 2017

(54) ADJUSTABLE PESSARY DEVICE AND METHOD

(71) Applicant: AMS Research Corporation, Minnetonka, MN (US)

(72) Inventors: Benjamin Y. Arcand, Minneapolis, MN (US); Justin H. Huelman, Lino Lakes, MN (US); Janet L. DeMarchi, Minnetonka, MN (US)

(*) Notice: Subject to any disclaimer, the term of this patent is extended or adjusted under 35 U.S.C. 154(b) by 174 days.

(21) Appl. No.: 14/056,805

(22) Filed: Oct. 17, 2013

(65) Prior Publication Data

US 2014/0107402 A1 Apr. 17, 2014

Related U.S. Application Data

(60) Provisional application No. 61/714,936, filed on Oct. 17, 2012.

(51) Int. Cl.
*A61F 2/00* (2006.01)
*A61F 6/08* (2006.01)

(52) U.S. Cl.
CPC ............. *A61F 2/005* (2013.01); *A61F 6/08* (2013.01)

(58) Field of Classification Search
CPC ...... A61F 2/0036; A61F 2/005; A61F 2/0009; A61F 2/04; A61F 6/08; A61F 2250/0007; A61F 2250/0031; A61F 2002/047; A61F 2/004; A61F 2250/0002; A61F 2/0027; A61F 2/0045; A61B 2017/00805
See application file for complete search history.

(56) References Cited

U.S. PATENT DOCUMENTS

| | | | |
|---|---|---|---|
| 2008/0033230 A1* | 2/2008 | Bartning et al. | 600/29 |
| 2008/0281149 A1* | 11/2008 | Sinai | A61F 2/005 600/32 |
| 2012/0136199 A1* | 5/2012 | Hou | A61F 2/005 600/29 |

\* cited by examiner

*Primary Examiner* — Christine H Matthews
(74) *Attorney, Agent, or Firm* — Brake Hughes Bellermann LLP

(57) ABSTRACT

Various embodiments of an adjustable pessary device are provided. The device can include an elastic ribbon or band, such as Nitinol, encapsulated in a soft or flexible structure, such as a rubber shell. In addition to providing a conforming, comfortable shape, the rubber layer can have additional structures to interface and fit with the anatomical structures within the vagina.

20 Claims, 4 Drawing Sheets

ADJUSTABLE PESSARY DEVICE AND METHOD

PRIORITY

This Application claims priority to and the benefit of U.S. Provisional Patent Application No. 61/714,936, filed Oct. 17, 2012, which is incorporated herein by reference in its entirety.

FIELD OF THE INVENTION

The present invention relates generally to treatment methods and apparatus and, more specifically, to an adjustable pessary device for use in treating incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

In certain cases, a pessary device is used to help support the uterus, vagina, bladder or rectum. Vaginal pessary devices can push the bladder neck up against the pelvic bone, holding it in place to mimic the natural sphincter mechanism. However, conventional pessary devices can be ill-suited for a patient's unique anatomical shapes and sizes. Further, conventional pessary devices are not readily adjustable without replacing the device or seeking a physician consultation.

There is a desire to obtain a minimally invasive yet highly effective and adjustable pessary device.

SUMMARY OF THE INVENTION

The present invention describes an adjustable pessary for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

The adjustable and flexible nature of the device reduces the issues of device sizing, or requiring multiple device sizes. This, in turn, opens up the potential for an individual patient to purchase and use the device in privacy without the need to consult with a physician.

Embodiments of the pessary device provide a multi-directional shape-changing construct. While in the open or deployed configuration, the device has a generally open oval-like shape and a generally S-shaped configuration when viewed from the side, e.g., 90 degrees around the long axis of the oval viewpoint. When the sides of the oval are squeezed together, the S-shape simultaneously reduces to a generally linear configuration. This greatly simplifies insertion, adjustment or placement while inserted, and removal of the device. Further, the shape memory nature of the device helps to conform to the appropriate location in the vagina. The distal portion of the S-shape naturally points anteriorally and can sit in the space adjacent to the cervix called the anterior fornix. Continence is achieved by one portion of the device—e.g., the proximal curve of the S-shape, protruding into the bladder neck and pubic symphysis. Additional support can be provided by the proximal end of the S-shape protruding in the direction of the perineal body.

The pessary device can include an undulating elastic ribbon provided therein. The elastic ribbon can be composed of various materials, including stainless steel, Nitinol, polymer, and the like. The device can be composed of two ribbons bonded face-to-face at either end. Between the ends, the ribbon can be twisted about its axis at least one turn, with the ribbons twisted in opposite directions. This combination provides a simple and unique method for providing the shape change characteristic of the device. Additionally, the ribbon wire or band can be set into a variety of shapes to alter the overall shape of the device.

The underlying elastic ribbon or band is generally encapsulated in a soft or flexible structure, such as a rubber shell structure. In addition to providing a conforming, comfortable construct, the rubber layer can have additional structures to interface and fit with the anatomic structures with the vagina. For instance, ends of the device might have wedge or saddle-shaped rubber ends to fit the fornix or perineal body.

As a self-administered device, the device can have the advantage of allowing an individual to evaluate and treat their SUI without the embarrassment of a physician consultation. This can open up SUI therapy to a large group of women that currently do not seek treatment. In addition, the device can be packaged with educational materials to inform the purchaser of permanent solutions such as SUI slings.

Figure 1A:
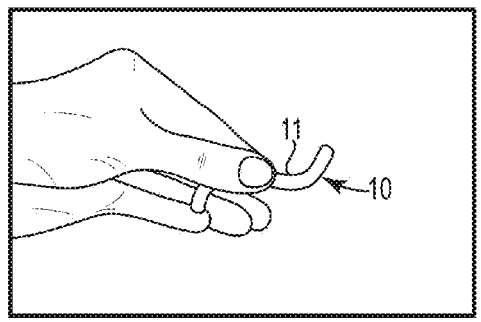
FIGS. 1A-1D are views an adjustable shape-memory pessary device in various stages of manipulation and insertion, in accordance with embodiments of the present invention.
Figure 1B:
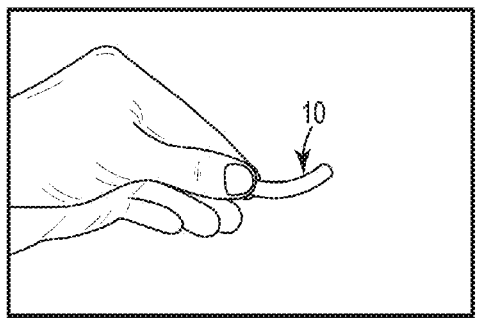
Figure 1C:
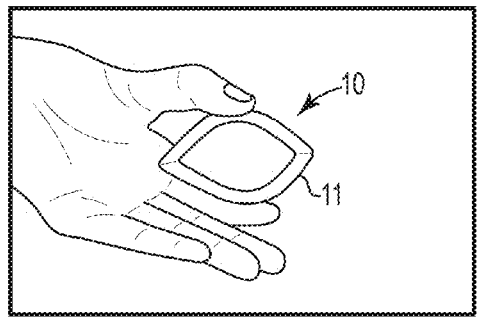
Figure 1D:
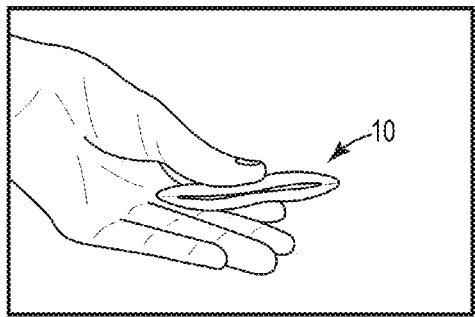
Figure 2:
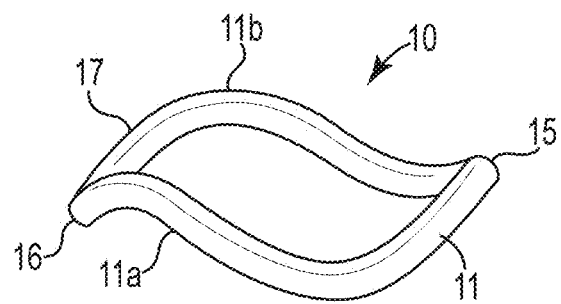
FIG. 2 is a perspective view of an adjustable shape-memory pessary device, in accordance with embodiments of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION OF PREFERRED EMBODIMENTS

Referring generally to FIGS. 1-6, various embodiments of a self-adjusting, conformable pessary device 10 are disclosed. In general, the pessary device 10 can include a generally soft, flexible outer housing 11, and an elastic wire, ribbon or band 12 encapsulated or otherwise provided within the housing 11—e.g., within a housing lumen. The outer housing 11 can include first and second undulating housing members 11a, 11b (unitary or separate). The elastic ribbon 12 can be composed of various materials including stainless steel, Nitinol, polymer, and the like. In various embodiments, the ribbon 12 is constructed of a shape-memory material, and can take on an undulating shape. The device 10 can be composed of two (e.g., first and second) undulating ribbons or ribbon portions 12a, 12b, bonded face-to-face at either end, or two or more ribbons 12 attached or provided adjacent (e.g., but not necessarily bonded) to one another. In other embodiments, the ribbon portions 12a, 12b are constructed of a single member and formed or otherwise provided in the desired shape.

Figure 4:
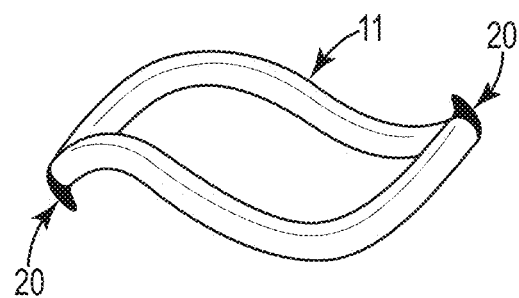
FIG. 4 is a perspective view of an adjustable shape-memory pessary device having end saddle-like portions, in accordance with embodiments of the present invention.

The outer housing 11 can be a flexible structure, such as a rubber structure (e.g., latex). In addition to providing a conforming, comfortable shape, the rubber layer 11 can have additional structures to interface and fit with the anatomical structures within the vagina. For instance, one or more ends 20 of the device 10 might have wedge or saddle-shaped rubber ends to fit the fornix or perineal body (FIG. 4).

Figure 3:
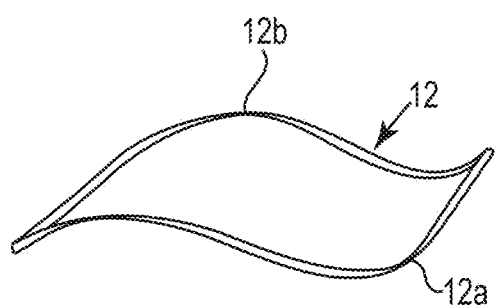
FIG. 3 is a perspective view of an inner undulating band of an adjustable pessary device, in accordance with embodiments of the present invention.

Between the ends, the ribbon 12 can be twisted about its axis at least one turn, with each ribbon portion 12a, 12b (face-to-face ribbons) twisted and oriented in opposing directions (FIG. 3). This configuration provides a simple and unique device and method for providing shape changing characteristics to facilitate adjustability. Further, the ribbon wire or band 12 can be set or otherwise formed into a variety of shapes and sizes to alter the overall shape of the device to address and treat various continence goals and patient anatomical structures. In addition, the shape memory and flexible nature of the device 10 permits easy readjustment during insertion to better ensure proper placement and orientation.

Embodiments of the pessary device 10 provide a multi-directional shape-changing construct. While in the open or deployed configuration, the device 10 has a generally open oval-like, or lily-like, shape (FIGS. 1A-1C, 2). The device has a generally S-shaped configuration when viewed from the side, e.g., 90 degrees around the long axis of the oval viewpoint (FIG. 1A). When the sides of the oval are squeezed together (FIG. 1D) during insertion, the S-shape reduces or otherwise deforms to a generally linear configuration, which provides the insertion and removal configuration for the device 10. Upon reaching the desired location as described herein, the shape memory nature of the device 10 causes it to generally rebound to its original shape and provide the desired support to treat incontinence.

Figure 6:
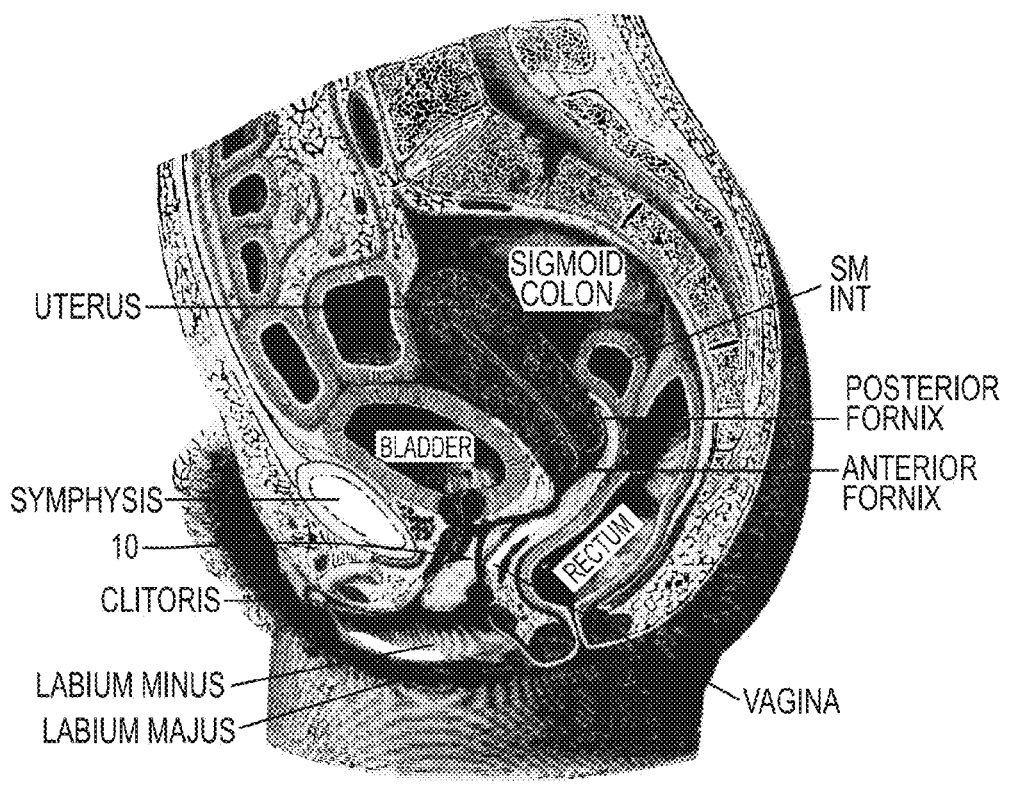
FIG. 6 is a schematic view of anatomical structure illustrating placement of an adjustable pessary device, in accordance with embodiments of the present invention.

The shape change or memory nature of the device 10 helps to conform to the appropriate target location in the vagina. A distal portion 15 of the S-shape naturally points anteriorally and sits in the space adjacent to the cervix called the anterior fornix. Continence is achieved by one portion of the device 10, e.g., such as a proximal curve 17 of the S-shape, protruding into the bladder neck and pubic symphisis (FIG. 6). Additional support is provided by a proximal end 16 of the S-shape protruding in the direction of the perineal body.

Figure 5:
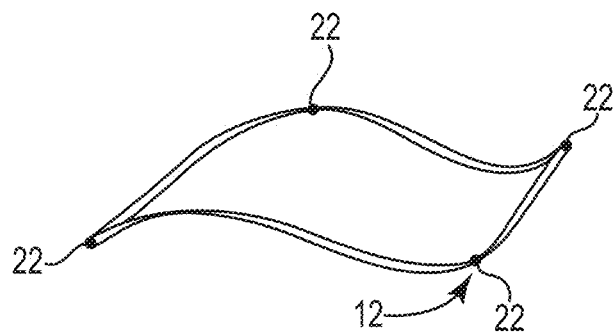
FIG. 5 is a perspective view of an inner undulating band of an adjustable pessary device having hinges, in accordance with embodiments of the present invention.

Other embodiments can include portions 12a, 12b connected by hinges 22, with one hinge 22 provided at each curve or like change or transition on the S-shape portion 12a, 12b, as shown in FIG. 5. With such embodiments, a total of four hinges can be included. Other embodiments can include more or less than four hinges to facilitate adjustability, manipulation, deployment and seating of the device 10 within the patient. The hinges 22 can take on various constructs. For instance, certain embodiments can include living hinges, pin hinges, crimps or bends in the portions 12a, 12b, ball hinges, and the like.

Certain embodiments of the device 10 can be used to evaluate the required sling tension necessary to adequately control the patient's stress urinary incontinence. This can be accomplished with a pessary device 10 that has a calibrated elasticity to provide a known pressure on the bladder neck, or a gauge that can be visualized (e.g., markings or indicia) in the proximal portion of the device. One or more of these devices 10 can be inserted until it is determined which device 10 provides the desired support on the bladder neck. Based on the known elasticity or visual information provided with the device 10, a sling or like implant device can be chosen to address the corresponding support needs indicated with the device 10 to promote continence.

Various other embodiments of the pessary device 10 can be used to elute a therapeutic agent or substance to aid in SUI treatment or prepare the tissues for optimal sling placement. For instance, an estrogen therapy release can be included, such as a coating or material included with the device or on a device surface, to increase the tissue thickness of the vaginal wall to reduce the likelihood of mesh erosion. In another example, an anti-muscarinic compound can elute from the device 10 (e.g., coating or added material to the device) to control an overactive bladder in mixed incontinence treatment.

Various methods and tools for introducing or deploying the devices or systems of the present invention can be used with the present invention as well. Further, the device and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A conformable medical device for treating incontinence, comprising:
   a flexible outer housing; and
   an inner band including two elastic undulating ribbon members disposed within the flexible outer housing, the two elastic undulating ribbon members having substantially the same shape and operably connected at first and second end portions, the first end portion having a first tip portion angling away from the two elastic undulating ribbon members in a first direction, the second end portion having a second tip portion angling away from the two elastic undulating ribbon member in a second direction, the second direction being different from the first direction, the device being insertable within a patient's vagina to treat incontinence.

2. The device of claim 1, wherein the outer housing includes a lumen to receive the inner band.

3. The device of claim 1, wherein the outer housing is constructed of a rubber material.

4. The device of claim 1, wherein at least one of the two elastic undulating ribbon members is twisted along its axis.

5. The device of claim 1, wherein at least one of the two elastic undulating ribbon members are twisted at least one full turn along their length.

6. The device of claim 1, wherein the inner band is constructed of a polymer material.

7. The device of claim 1, wherein the inner band is constructed of a Nitinol material.

8. The device of claim 1, wherein the inner band is constructed of a stainless steel material.

9. The device of claim 1, wherein the inner band is generally S-shaped.

10. The device of claim 1, wherein the second direction is opposite to the first direction.

11. An adjustable pessary device to treat incontinence, comprising:
    a flexible outer housing including a first undulating member and a second undulating member; and
    an inner band including first and second undulating ribbon members, the first undulating ribbon member disposed within the first undulating member of the outer housing and the second undulating ribbon member disposed within the second undulating member of the outer housing, such that the first and second undulating ribbon members are operably joined at first and second end portions, the first and second end portions having tip portions angling away from the first and second undulating ribbon members in opposite directions, for insertion within a patient's vagina to treat incontinence.

12. The device of claim 11, wherein the outer housing is constructed of a rubber material.

13. The device of claim 11, wherein the first and second undulating ribbon members are constructed of a shape-memory material.

14. The device of claim 11, wherein the first and second undulating ribbon members are twisted at least one full turn along their respective lengths.

15. The device of claim 14, wherein the first and second undulating ribbon members each twist in opposing directions.

16. The device of claim 11, wherein the inner band is constructed of a polymer material.

17. The device of claim 11, wherein the inner band is constructed of a Nitinol material.

18. The device of claim 11, wherein the inner band is constructed of a stainless steel material.

19. The device of claim 11, wherein at least one of the first and second undulating ribbon members is generally S-shaped.

20. The device of claim 11, wherein the outer housing is at least in part generally S-shaped.

* * * * *